United States Patent
Burzynski

(10) Patent No.: US 6,943,192 B2
(45) Date of Patent: Sep. 13, 2005

(54) TREATMENT REGIMEN FOR ADMINISTRATION OF PHENYLACETYLGLUTAMINE, PHENYLACETYLISOGLUTAMINE, AND/OR PHENYLACETATE

(76) Inventor: Stanislaw R. Burzynski, 20 W. Rivercrest, Houston, TX (US) 77042

( * ) Notice: Subject to any disclaimer, the term of this patent is extended or adjusted under 35 U.S.C. 154(b) by 8 days.

(21) Appl. No.: 09/863,035

(22) Filed: May 22, 2001

(65) Prior Publication Data

US 2001/0044466 A1 Nov. 22, 2001

Related U.S. Application Data

(62) Division of application No. 09/121,567, filed on Jul. 23, 1998, now Pat. No. 6,258,849.

(51) Int. Cl.[7] .............................................. A61K 31/195
(52) U.S. Cl. ........................ 514/561; 514/563; 514/568; 514/569
(58) Field of Search ................................. 514/561, 563, 514/568, 565

(56) References Cited

U.S. PATENT DOCUMENTS

| 4,284,647 A | | 8/1981 | Brusilow ..................... 424/317 |
| 4,470,970 A | | 9/1984 | Burzynski ................... 424/177 |
| 5,244,922 A | * | 9/1993 | Burzynsky .................. 514/561 |
| 5,254,587 A | | 10/1993 | Burzynski ................... 514/563 |
| 5,605,930 A | | 2/1997 | Samid ......................... 514/510 |

FOREIGN PATENT DOCUMENTS

| WO | WO 93 24123 | 12/1993 |
| WO | WO 97 42939 | 11/1997 |

OTHER PUBLICATIONS

Carter et al., Chemotherapy of Cancer, 2nd edition, John Wiley & Sons, NY, NY, 1981, pp356, and 362–365.*
Burzynski et al., "Toxicology Studies on Antineoplaston AS2–1 Injections in Cancer Patients," *Drugs. Exptl. Clin. Res.*, Suppl. 1, XII:25–35 (1986).
Burzynski et al., "Preclinical Studies on Antineoplaston AS2–1 and Antineoplaston AS2–5," *Drugs. Exptl. Clin. Res.*, Suppl. 1, XII:11–16 (1986).
Prados et al., "Protocol NABTC 9402: Phase II Trial of Phenylacetic Acid for Recurrent Malignant Glioma," http://cc.ucsf.edu/Pr/NATBTC_9402.pr.html, pp. 1–13 (Aug. 29, 1996).
Buckner et al., "Phase II Study of Antineoplastons A10 (NSC 648539) and AS2–1 (NSC620261) in Patients with Recurrent Glioma", Mayo Clinic Proceedings, vol. 74, No. 2, Feb. 1, 1999, pp. 137–145.

Chang et al, "Phase II Study of Pheylacetate in Patients with Recurrent Malignant Glioma: A North American Brain Tumor consortium Report", Journal of Clinical Oncology, vol. 17, No. 3, Mar. 1999, pp. 984–990.
Thibault et al, "Phase I Study of Pheylacetate Administered Twice Daily to Patients with Cancer", CANCER, vol. 75, 1995, pp. 2932–2938.
Thibault et al, "A Phase I Study of the Differentiating Agent Phenyl Utyrate in Patients with Cancer", Annals of Oncology, vol. 7, No. s1, 1996, p. 63.
Piscitelli, Stephen C. et al, "Disposition of Phenylbutyrate and its metabolites, phenylacetate and phenylacetylglutamine", J. Clin. Pharmacol. (1995), 35(4), 368–73.
Burzynski and Kubove, "Toxicology Studies on Antineoplastic A10 Injections in Cancer Patients", Drugs Exptl. Clin. Res., vol. 12 No. s1, 1986, pp. 47–55.
Burzynski, Toxicology Studies on Antineoplaston AS2–5 Injections in Cancer Patients:, Drugs Eptl. Clin. Res., vol. 12, No. s1, 1986, pp. 17–24.
Ashraf et al. *"Preclinical Studies on Antineoplaston A10 Injections"; Drugs. Exptl. Clin. Res.*; Suppl. 1, XII, 37–45 (1986).
Tsuda et al., *"Inhibitory Effect of Antineoplaston A10 and AS2–1 on Human Hepatocellular Carcinoma"; The Kurume Medical Journal*; (1996) vol. 43:137–147.
Waldbillig, Robert, J., *"Pharmicokinetics of Antineoplaston A–10 and AS2–1 in patients with neoplastic disease"* Report filed with FDA Mar. 14, 1997.
Waldbillig, RJ, Patil, S, and Burzynski, SR *"Uptake and intracellular binding of the antineoplastic agents phenylacetic acid (PN) and phenylacetylglutamine (PG): Effects on epigenetic mechanisms of gene regulation and gene expression"*, Report filed with FDA on May 26, 2004.
Burzynski, Janicki, Weaver, Jurida, Szymmkowski, Khan and Dolgopolov, *"Clinical application of body epigenetic system: multi–targeted therapy for primary brain tumors"* Poster at the World Conference on Dosing of Antiinfectives, Nurenberg, Germany, Sep. 9–11, 2004.

* cited by examiner

*Primary Examiner*—Rebecca Cook
(74) *Attorney, Agent, or Firm*—Howrey Simon Arnold & White, LLP

(57) ABSTRACT

Herein is disclosed a method of treating neoplastic disease, including cancer, comprising administering a pharmaceutical composition, the pharmaceutical composition comprising a highly concentrated aqueous solution of phenylacetylglutamine and phenylacetylisoglutamine in a 4:1 ratio, at an infusion rate of from 100 mL/hr to 400 mL/hr. In a further embodiment, herein is also disclosed a method of treating neoplastic disease, including cancer, comprising administering a pharmaceutical composition, the pharmaceutical composition comprising a highly concentrated aqueous solution of phenylacetate and (phenylacetylglutamine or phenylacetylisoglutamine) in a 4:1 ratio, at an infusion rate of from 100 mL/hr to 400 mL/hr. Herein are also disclosed the pharmaceutical compositions used in the above methods.

16 Claims, No Drawings

TREATMENT REGIMEN FOR ADMINISTRATION OF PHENYLACETYLGLUTAMINE, PHENYLACETYLISOGLUTAMINE, AND/OR PHENYLACETATE

This application is a division of patent application Ser. No. 09/121,567 filed Jul. 23, 1998 now U.S. Pat. No. 6,258,849.

BACKGROUND OF THE INVENTION

1. Field of the Invention

The present invention relates generally to the field of neoplastic disease treatment. More particularly, it concerns the intravenous administration of highly concentrated solutions of phenylacetylglutamine and phenylacetylisoglutamine, or phenylacetylglutamine and phenylacetate, or salts or derivatives thereof, at high infusion rates and high dosage levels.

2. Description of Related Art

Research on growth factors and growth inhibitors during the last thirty years indicates the possible existence of a defense system of the human body complementary to the immune system. This defense system of differentiation inducers and regulators of oncogene and tumor-suppressor-gene expression may be termed a "biochemical defense system" or "BDS." Whereas the main purpose of the immune system is protection of the body against external invasion, the main purpose of the BDS is protection of the body against defective cells. Human neoplastic diseases (cancers, malignant and benign tumors) are examples of diseases that can be combated by the BDS. One class of compounds that provide components of the BDS are naturally-occurring amino acid analogs and carboxylic acids.

Though not to be bound by theory, the mechanism of defense against cancers by naturally-occurring amino acid analogs can be induction of differentiation, conjugation of glutamine to inhibit growth of cancerous cells, downregulation of oncogenes such as ras, or upregulation of detoxification genes such as GSTP1 and GSTM1 and tumor suppressor genes such as p53, retinoblastoma gene, and neurofibromatosis gene type 1, possibly by decreasing methylation of hypermethylated genes. Regardless of the detailed mechanism of action, naturally-occurring amino acid analogs are known to induce abnormal cells to undergo terminal differentiation and die through programmed cell death. Unlike necrosis associated with chemotherapy or radiation therapy, dying cells are gradually eliminated and replaced by normal cells, leading to organ healing and reconstruction of function.

The study of naturally-occurring amino acid analogs as potential anti-cancer agents, hereinafter generally "antineoplastons," began in 1967 with the observation of significant deficiencies in the serum peptide content of cancer patients. During the 1980's, the isolation of antineoplaston fractions from human urine and the use of these fractions in the treatment of human cancers were taught by Burzynski, U.S. Pat. No. 4,470,970, the entire specification of which is incorporated by reference herein. Among the compositions put forth as cancer treatments were (a) 3-phenylacetylamino-2,6-piperidinedione, and (b) a mixture of sodium phenylacetate and phenylacetylglutamine in a 4:1 ratio by mass. Composition (b) may hereinafter be referred to as "antineoplaston AS2-1" or simply "AS-2-1." 3-phenylacetylamino-2,6-piperidinedione was discovered to hydrolyze during treatment with sodium hydroxide upon dissolving and neutralization to phenylacetylglutamine and phenylacetylisoglutamine in a 4:1 ratio.

Formulations of the above compositions were prepared and had successful preclinical activity. 3-phenylacetylamino-2,6-piperidinedione produced a cytostatic effect on cultured human breast cancer cell line MDA-MB-231. Dose-dependent inhibition of the growth curves of cell lines KMCH-1, KYN-1, and KIM-1; rat Nb2 lymphoma; and human colon adenocarcinoma was also observed upon administration of 3-phenylacetylamino-2,6-piperidinedione.

In vivo experiments were performed in which 3phenylacetylamino-2,6-piperidinedione, or A10, was administered to mice implanted with S180 cells or R-27 human breast cancer cells. In the S180 experiment, cAMP levels in the livers and tumors of treated mice were significantly elevated relative to control mice after administration of 3-phenylacetylamino-2,6-piperidinedione. In the R-27 experiment, $^3$H-TdR uptake inhibition and growth curve inhibition were observed after injection of A10.

AS-2-1 or phenylacetic acid produced dose-dependent growth inhibition in breast carcinoma cell line HBL-100 and Ki-1, and also promoted terminal differentiation or phenotypic reversion in cell lines of human promyelocytic leukemia HL-60, chronic lymphocytic leukemia, neuroblastoma, murine fibrosarcoma V7T, hormonally refractory prostate adenocarcinoma PC3, astrocytoma, medulloblastoma, malignant melanoma and ovarian carcinoma. AS2-1 or phenylacetic acid caused adipocyte conversion in cultured premalignant mesenchymal C3H 10T1/2 cells and enhanced hemoglobin production in K562 erythroleukemia cells. Further, and in distinction to then-current standard chemotherapeutic agents such as 5-aza-2-deoxycitidine, phenylacetic acid did not cause tumor progression in premalignant C3H 10T1/2 cells.

Preclinical toxicology studies determined that the $LD_{50}$ for A10 in mice was 10.33 g/kg/day. Autopsy of animals which died revealed generalized congestion of the viscera, pulmonary edema, and hemorrhagic changes in the alveoli. In autopsy, surviving test animals were identical to control animals. Chronic toxicity studies revealed no negative effects after 180 days.

The $LD_{50}$ for AS2-1 in mice was 2.83 g/kg/day. Autopsy of animals which died revealed generalized congestion of the viscera, pulmonary edema, and hemorrhagic changes in the alveoli, as well as Tardieu's spots and congestion of the thymus. Chronic toxicity studies using up to 1.11 g/kg/day revealed no negative effects after 365 days.

A10 and AS2-1 were observed to be non-mutagenic by the Ames method, and A10 was observed to be non-teratogenic in rat fetuses.

A noteworthy point regarding the toxicology studies is that phenylacetylglutamine, a component of AS2-1 and also a breakdown product of 3-phenylacetylamino-2,6-piperidinedione, is not normally found in mice but is normally found in humans. This suggests that humans might exhibit greater tolerance of both A10 and AS2-1 than do mice, and thus higher doses of both compositions might be possible in humans. This suggestion is accurate as will be shown below.

In human toxicity studies in Phase I clinical trials, intravenous administration of A10 at dosages up to 2.21 g/kg/day was associated with minimal side effects, including febrile reaction, muscle and joint pain, muscle contraction in the throat, abdominal pain of short duration, and single incidences of nausea, dizziness, and headache (*Drugs Exptl Clin Res* 1986, 12 Suppl 1, 47–55).

Oral administration of AS2-1 at dosages up to 238 mg/kg/day was associated with a temporary mild decrease in white blood cell count in one patient. Injection of AS2-1 at dosages up to 160 mg/kg/day was associated with minimal side effects, including slight nausea and vomiting, allergic skin reaction, moderate elevation of blood pressure, febrile reaction, mild decrease in white blood cell count, (one patient each) and mild electrolyte imbalance in three patients.

Clinical trials determined that 3-phenylacetylamino-2,6-piperidinedione, A10, and AS2-1 were effective in treating cancer. Burzynski et al. (*Drugs Exptl. Clin. Res.* 12 Suppl. 1, 25–35 (1986)) reported that an intravenous solution of antineoplaston AS2-1 (100 mg/mL active ingredients) was injected into patients at dosages of not more than 0.16 g/kg/day. Of 21 cases of neoplastic disease, observed were six complete remissions, two partial remissions, seven stabilizations, and six cases of progressive disease.

Phase II clinical trials were conducted wherein patients suffering from astrocytomas were infused with A10 (100 mg/mL) at dosage levels of from 0.5 to 1.3 g/kg/day or with AS2-1 (100 mg/mL) at dosage levels of from 0.2 to 0.5 g/kg/day for from 67 to 706 days (in: *Recent Advances in Chemotherapy*, Adam, D., ed. Munich: Futuramed, 1992). Of 20 patients, four experienced complete responses, two experienced partial responses, ten experienced stabilizations, and four experienced progressive disease.

In Samid, U.S. Pat. No. 5,605,930 (the entire content of which is incorporated by reference herein), sodium phenylacetate alone was used in treating human cancers, and was administered in dosages of not more than 0.3 g/kg/day. However, a number of shortcomings of the low concentrations, flow rates, and dosages of the intravenous solutions were observed.

First, Burzynski et al. (*Drugs Exptl. Clin. Res.* 12 Suppl. 1, 11–16 (1986)) reported complete colony reduction of HBL-100 and Ki No. 1 tumor cell lines with 5.0 mg/mL of either phenylacetic acid or antineoplaston AS2-1. Similarly, cytostasis was observed for human breast carcinoma cell line MDA-MB-231 using concentrations of 3-phenylacetylamino-2,6-piperidinedione of 2.0 mg/mL and AS2-1 of 3.0 mg/mL. However, 3-phenylacetylamino-2,6-piperidinedione is poorly soluble in water, and when orally administered to rats the peak plasma level is approximately 0.2 mg/mL, roughly 10-fold less than the cytostatic concentration observed in tissue culture experiments. Under typical administration regimes of antineoplaston AS2-1, the peak plasma levels of phenylacetic acid are approximately 0.43 mg/mL, roughly 7-fold less than the cytostatic concentration observed in tissue culture experiments. Also, both 3-phenylacetylamino-2,6-piperidinedione, its hydrolysis products, and AS2-1 are rapidly cleared in vivo.

Also, during uptake of antineoplastons by tumor tissue, a concentration gradient forms between the outside of the tumor tissue, at which the concentration of antineoplaston will be equal to the plasma concentration, and a point or points in the interior of the tumor tissue, at which the concentration of antineoplaston will be at a minimum, and may be zero. Relatively low plasma concentrations of anti-cancer agents therefore lead to some inner portion of the tumor tissue avoiding significant uptake of the anti-cancer agent and remaining in its cancerous state.

Second, administration of a solution comprising the hydrolysis products of 3-phenylacetylamino-2,6-piperidinedione at low infusion rates of from 2.5 mL/h to 84 mL/h frequently results in an elevation in levels of waste products in plasma. An exemplary waste product so elevated is uric acid. This elevation interferes with treatment by requiring either a decrease in the dose or an interruption in the treatment to administer additional drugs, for example, Allopurinol, to decrease the level of the waste product, for example, uric acid.

Therefore, it is desirable to have intravenous formulations of pharmaceutical compositions of amino acid analogs with anti-cancer activity wherein the intravenous formulations provide high plasma concentrations of the active ingredient or ingredients in order to fully penetrate tumors with effective amounts of the active ingredient or ingredients. It is also desirable that such intravenous formulations do not lead to elevated levels of waste products in plasma.

SUMMARY OF THE INVENTION

The present invention relates to a method of treating neoplastic disease, including cancer, comprising administering a pharmaceutical composition to a patient, the pharmaceutical composition comprising a phenylacetylglutamine compound of Formula I and a phenylacetylisoglutamine compound of Formula III. The compound of Formula I is present in a 4:1 weight ratio to a phenylacetyl-isoglutamine compound of Formula III.

Formula I is represented by the structure:

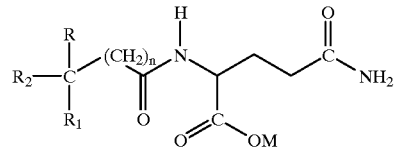

wherein R and $R_1$ are independently selected from the group consisting of H, lower alkoxy ($C_{1-6}$), or lower alkyl ($C_{1-6}$); $R_2$ is selected from the group consisting of aryl ($C_{6-12}$) and substituted aryl; M is hydrogen, a salt forming cation, such as sodium, potassium, or ammonium, diethanolamine, cyclohexylamine, a naturally-occurring amino acid of MW less than 500 kD, lower alkyl ($C_{1-6}$), cycloalkyl, or aryl ($C_{6-12}$); and n is 0–5. Preferably, M is hydrogen or sodium; n is 0; R is selected from the group consisting of H and $C_3H_7$; $R_1$ is selected from the group consisting of H, $CH_3$, $CH_3$—O—, $C_2H_5$, and $C_3H_7$; and $R_2$ is an aryl selected from the group consisting of Formula II:

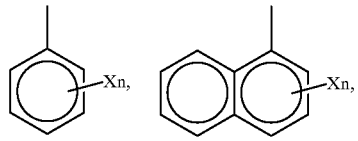

Formula II wherein X is a halogen, lower alkyl ($C_{1-6}$), lower alkoxy ($C_{1-6}$), cycloalkyl, cycloalkoxy, aryl ($C_{6-12}$), substituted aryl or hydroxy and n is 0, 1, 2, 3, or 4. More preferably, $R_2$ is phenyl or selected from the group of Formula II, wherein X is selected from Cl, F, or OH. Most preferably, $R_2$ is phenyl or phenylchloride. Further, the compound of Formula I can be employed as a racemic mixture or as separate optic isomers or any combination thereof.

Formula III is represented by the structure:

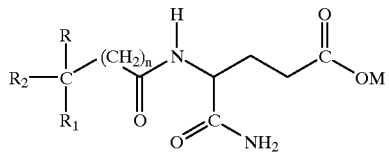

wherein R and $R_1$ are independently selected from the group consisting of H, lower alkoxy ($C_{1-6}$), or lower alkyl ($C_{1-6}$); $R_2$ is selected from the group consisting of aryl ($C_{6-12}$) and substituted aryl; M is hydrogen, a salt forming cation, such as sodium, potassium, or ammonium, diethanolamine, cyclohexylamine, a naturally-occurring amino acid of MW less than 500 kD, lower alkyl ($C_{1-6}$), cycloalkyl, or aryl ($C_{6-12}$); and n is 0–5. Preferably, M is hydrogen or sodium; n is 0; R is selected from the group consisting of H and $C_3H_7$; $R_1$ is selected from the group consisting of H, $CH_3$, $CH_3$—O—, $C_2H_5$, and $C_3H_7$; and $R_2$ is an aryl ($C_{6-12}$) or a substituted aryl selected from the group consisting of Formula II, wherein X is a halogen, lower alkyl ($C_{1-6}$), lower alkoxy ($C_{1-6}$), cycloalkyl, cycloalkoxy, aryl ($C_{6-12}$), substituted aryl or hydroxy and n is 0, 1, 2, 3, or 4. More preferably, $R_2$ is phenyl or a substituted aryl of Formula II, wherein X is selected from Cl, F, or OH. Most preferably, $R_2$ is phenyl or phenylchloride. Likewise, the compound of Formula III can be used as a racemic mixture or as separate optic isomers or any combination thereof.

In the composition, the combined concentration of the phenylacetylglutamine compound of Formula I and the phenylacetylisoglutamine compound of Formula III in an aqueous solution is from about 200 mg/mL to about 350 mg/mL, and the composition is administered at an infusion rate of from 2.5 mL/h to 400 mL/h, preferably from 100 mL/h to 400 mL/h.

In a further embodiment, the present invention relates to a method of treating neoplastic disease, including cancer, comprising administering a pharmaceutical composition, the pharmaceutical composition comprising a phenylacetic acid compound of Formula IV:

Formula IV

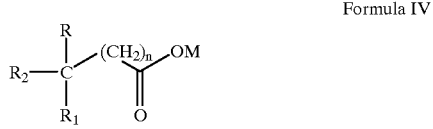

wherein R and $R_1$ are independently selected from the group consisting of H, lower alkoxy ($C_{1-6}$), or lower alkyl ($C_{1-6}$); $R_2$ is selected from the group consisting of aryl ($C_{6-12}$) and substituted aryl; M is hydrogen, a salt forming cation, such as sodium, potassium, or ammonium, diethanolamine, cyclohexylamine, a naturally-occurring amino acid of MW less than 500 kD, lower alkyl ($C_{1-6}$), cycloalkyl, or aryl ($C_{6-12}$); and n is 0–5. Preferably, M is hydrogen or sodium; n is 0; R is selected from the group consisting of H and $C_3H_7$; $R_1$ is selected from the group consisting of H, $CH_3$, $CH_3$—O—, $C_2H_5$, and $C_3H_7$; and $R_2$ is an aryl selected from the group consisting of Formula II, wherein X is a halogen, lower alkyl ($C_{1-6}$), lower alkoxy ($C_{1-6}$), cycloalkyl, cycloalkoxy, aryl ($C_{6-12}$), substituted aryl or hydroxy and n is 0, 1, 2, 3, or 4. More preferably, $R_2$ is phenyl or a substituted aryl selected from the group of Formula II, wherein X is selected from Cl, F, or OH. Most preferably, $R_2$ is phenyl or phenylchloride.

In another embodiment, the compound of Formula IV is present in a 4:1 ratio by weight to a compound of Formula I, typically in an aqueous solution. In the composition, the combined concentration of the compound of Formula I and the compound of Formula IV is from about 70 mg/mL to about 150 mg/mL, and the composition is administered at an infusion rate of from 2.5 mL/hr to 400 mL/hr, preferably 100 mL/hr to 400 mL/hr.

In yet another embodiment, the present invention relates to a pharmaceutical composition, comprising a compound of Formula IV in a 4:1 ratio to a compound of Formula III, wherein the combined concentration of the compound of Formula IV and the compound of Formula III is from about 200 mg/mL to about 350 mg/mL, and the composition is administered at an infusion rate of from 2.5 mL/hr to about 400 mL/hr, preferably 100 mL/hr to 400 mL/hr.

These flow rates are far higher than any known to be previously reported for anti-cancer agents. High flow rates are beneficial in treating cancer because they allow the reaching of blood concentrations of the active agents of antineoplaston A10 roughly twice as high as with conventional lower infusion rates. High flow rates allow reaching of concentrations in the blood which are comparable to those shown to have anti-cancer activity in tissue culture, and also allow superior penetration of tumor tissue. High flow rates are therefore more efficacious than lower infusion rates in the treatment of cancer.

DESCRIPTION OF ILLUSTRATIVE EMBODIMENTS

As used hereinafter, the term "antineoplaston A10" is defined as a mixture of the sodium salts of phenylacetylglutamine and phenylacetylisoglutamine in a 4:1 ratio.

As used herein, the terms "antineoplaston AS2-1" and "AS2-1" are defined as a mixture of the sodium salts of phenylacetic acid and phenylacetylglutamine in a 4:1 ratio.

As used herein, the term "patient" includes human and veterinary patients.

The invention will be described in terms of preferred embodiments known at the time of filing this application which represent the best mode currently contemplated for making and using the pharmaceutical compositions of the present invention in the methods of the present invention.

A. Preparation of Pharmaceutical Compositions

Pharmaceutical compositions of the present invention comprise, in one embodiment, a compound of Formula I:

Formula I

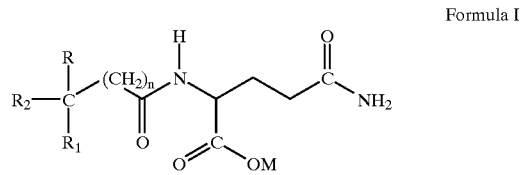

wherein R and $R_1$ are independently selected from the group consisting of H, lower alkoxy ($C_{1-6}$), or lower alkyl ($C_{1-6}$); $R_2$ is selected from the group consisting of aryl ($C_{6-12}$) and substituted aryl; M is hydrogen, salt forming cation, such as sodium, potassium, ammonium, diethanolamine, cyclohexylamine, or a naturally-occurring amino acid of MW less than 500 kD, alkyl ($C_{1-6}$), cycloalkyl, or aryl ($C_{6-12}$); and n is 0–5. Preferably, M is hydrogen or sodium; n is 0; R is selected from the group consisting of H and $C_3H_7$; $R_1$ is selected from the group consisting of H, CH$_3$, CH$_3$—O—, C$_2$H$_5$, and C$_3$H$_7$; and R$_2$ is an aryl (C$_{6-12}$) selected from the group consisting of Formula II:

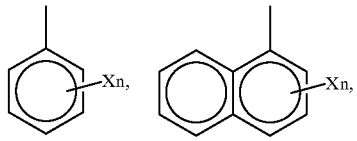

Formula II wherein X is a halogen, lower alkyl (C$_{1-6}$), lower alkoxy (C$_{1-6}$), cycloalkyl, cycloalkoxy, aryl (C$_{6-12}$), substituted aryl or hydroxy and n is 0, 1, 2, 3, or 4. More preferably, R$_2$ is phenyl or a substituted aryl selected from the group of Formula II, wherein X is selected from Cl, F, or OH. Most preferably, R$_2$ is phenyl or phenylchloride.

The compound of Formula I is present in a 4:1 ratio by mass to a compound of Formula III:

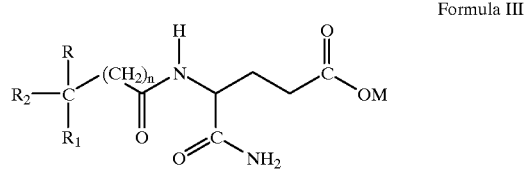

Formula III wherein R and R$_1$ are independently selected from the group consisting of H, lower alkoxy (C$_{1-6}$), or lower alkyl (C$_{1-6}$); R$_2$ is selected from the group consisting of aryl (C$_{6-12}$) and substituted aryl; M is hydrogen, salt forming cation, such as sodium, potassium, ammonium, diethanolamine, cyclohexylamine, or a naturally-occurring amino acid of MW less than 500 kD, alkyl (C$_{1-6}$), cycloalkyl, or aryl (C$_{6-12}$); and n is 0–5. Preferably, M is hydrogen or sodium; n is 0; R is selected from the group consisting of H and C$_3$H$_7$; R$_1$ is selected from the group consisting of H, CH$_3$, CH$_3$—O—, C$_2$H$_5$, and C$_3$H$_7$; and R$_2$ is an aryl selected from the group consisting of Formula II, wherein X is a halogen, lower alkyl (C$_{1-6}$), lower alkoxy (C$_{1-6}$), cycloalkyl, cycloalkoxy, aryl (C$_{6-12}$), substituted aryl or hydroxy and n is 0, 1, 2, 3, or 4. More preferably, R$_2$ is phenyl or a substituted aryl selected from the group of Formula II, wherein X is selected from Cl, F, or OH. Most preferably, R$_2$ is phenyl or phenylchloride.

In the composition, the combined concentration of the compound of Formula I and the compound of Formula III is from about 200 mg/mL to about 350 mg/mL. Typically, a racemic mixture of each compound will be used; however, the separate optic isomers can also be used.

In a second embodiment, pharmaceutical compositions of the present invention comprise an aqueous solution of a compound of Formula IV:

Formula IV wherein R and R$_1$ are independently selected from the group consisting of H, lower alkoxy (C$_{1-6}$), or lower alkyl (C$_{1-6}$); R$_2$ is selected from the group consisting of aryl (C$_{6-12}$) and substituted aryl; M is hydrogen, a salt forming cation, such as sodium, potassium, ammonium, diethanolamine, cyclohexylamine, or a naturally-occurring amino acid of MW less than 500 kD, alkyl (C$_{1-6}$), cycloalkyl, or aryl (C$_{6-12}$); and n is 0–5. Preferably, M is hydrogen or sodium; n is 0; R is selected from the group consisting of H and C$_3$H$_7$; R$_1$ is selected from the group consisting of H, CH$_3$, CH$_3$—O—, C$_2$H$_5$, and C$_3$H$_7$; and R$_2$ is an aryl selected from the group consisting of Formula II, wherein X is a halogen, lower alkyl (C$_{1-6}$), lower alkoxy (C$_{1-6}$), cycloalkyl, cycloalkoxy, aryl (C$_{6-12}$), substituted aryl or hydroxy and n is 0, 1, 2, 3, or 4. More preferably, R$_2$ is phenyl or a substituted aryl selected from the group of Formula II, wherein X is selected from Cl, F, or OH. Most preferably, R$_2$ is phenyl or phenylchloride.

The compound of Formula IV is present in a 4:1 ratio by mass to a compound of Formula I, and in the composition, the combined concentration of the compound of Formula I and the compound of Formula IV is from about 70 mg/mL to about 150 mg/mL.

In yet another embodiment of the invention, the compound of Formula IV is present in a 4:1 ratio by mass to a compound of Formula III, and in the composition, the combined concentration of the compound of Formula IV and the compound of Formula III is from about 70 mg/mL to about 150 mg/mL.

Preferred compounds are, of Formula I, phenylacetylglutamine and sodium phenylacetylglutamine and the L optic isomers thereof; of Formula III, phenylacetylisoglutamine and sodium phenylacetylisoglutamine; and of Formula IV, phenylacetic acid and sodium phenylacetate.

Phenylacetylglutamine can be isolated from human body fluids, for example, urine, or it can be synthesized by techniques known in the art, e.g. treatment of phenylacetic acid with N,N'-disuccinimidyl carbonate in acetonitrile followed by reaction with L-glutamine in the presence of a NaHCO$_3$ in a 1:1 acetonitrile/water mixture. Phenylacetylglutamine can also be synthesized by the reaction of phenylacetyl chloride with L-glutamine in the presence of NaHCO$_3$ in an aqueous solution. Yet another synthesis method that can be used is the treatment of 3-phenylacetylamino-2,6-piperidinedione with sodium hydroxide.

Phenylacetylisoglutamine can be synthesized by the reaction of phenylacetyl chloride with L-glutamine to yield phenylacetylglutamine, with subsequent heating under vacuum at 160° C. to yield 3-phenylacetylamino-2,6-piperidinedione, which can then be treated with sodium hydroxide. Also, phenylacetylisoglutamine can be prepared by treatment of phenylacetic acid with N,N'-disuccinimidyl carbonate in acetonitrile followed by reaction with L-isoglutamine in the presence of NaHCO$_3$ in a 1:1 acetonitrile/water mixture. However, the second synthesis requires L-isoglutamine, which is expensive, so the former route of synthesis is preferred on economic grounds.

Phenylacetic acid can be isolated from human body fluids, for example, urine, or it can be synthesized by techniques known in the art, such as refluxing benzyl cyanide with dilute sulfuric or hydrochloric acid.

Other compounds of Formulas I, III, and IV can be synthesized by techniques known in the art. For example, the acid addition salts can be generated from the free base forms of the compounds by reaction of the latter with one equivalent of a suitable nontoxic, pharmaceutically-acceptable acid, followed by evaporation of the solvent employed for the reaction and recrystallization of the salt, if required. The free base can be recovered from the acid addition salt by a reaction of the salt with a water solution of the salt with a suitable base such as sodium carbonate, sodium hydroxide, and the like.

"Pharmaceutically acceptable salts" means salts having the biological activity of the parent compound and lacking toxic activity at the selected administration level. Again, determination of whether a salt is pharmaceutically acceptable can be accomplished by methods known to those of skill in the art. Pharmaceutically acceptable salts of phenylacetylglutamine, phenylacetylisoglutamine, and phenylacetic acid include, but are not limited to, inorganic sodium, potassium and ammonium salts, and organic diethanolamine, cyclohexylamine, and amino acid salts. Preferably, the salt is a sodium salt.

Suitable acids for forming acid addition salts of the compounds of the present invention include, but are not limited to, acetic, benzoic, benzenesulfonic, tartaric, hydrobromic, hydrochloric, citric, fumaric, gluconic, glucuronic, glutamic, lactic, malic, maleic, methanesulfonic, pamoic, salicylic, stearic, succinic, sulfuric, and tartaric acids. The class of acids suitable for the formation of nontoxic, pharmaceutically-acceptable salts is well known to practitioners of the pharmaceutical formulation arts. (See, for example, Stephen N. Berge, et al. *J. Pharm. Sciences*, 66:1–19 (1977))

The compounds of the present invention can also exist in different stereoisomeric forms by virtue of the presence of one or more asymmetric centers in the compound. The present invention contemplates all stereoisomeric forms of the compounds as well as mixtures thereof, including racemic mixtures. Individual stereoisomers may be obtained, if desired, by methods known in the art as, for example, the separation of stereoisomers in chiral chromatographic columns.

Further, the compounds of the present invention can exist in unsolvated as well as solvated forms with pharmaceutically-acceptable solvents such as water, ethanol, and the like. In general, the solvated forms are considered equivalent to the unsolvated forms for the purposes of the present invention.

Precursors of phenylacetylglutamine, phenylacetylisoglutamine, and phenylacetic acid can be used in the present compositions. Precursors of phenylacetylglutamine, phenylacetylisoglutamine, and phenylacetic acid are hereby defined as compounds that can be metabolized to yield phenylacetylglutamine, phenylacetylisoglutamine, and phenylacetic acid in humans. Pharmaceutically-acceptable precursors of phenylacetylglutamine, phenylacetylisoglutamine, and phenylacetic acid are precursors which lack toxic activity at the selected administration level, either per se or as any metabolic intermediate between the precursor and the final compound. Determination of whether precursors of phenylacetylglutamine, phenylacetylisoglutamine, and phenylacetic acid are pharmaceutically acceptable can be achieved by application of methods known to those of skill in the art. A preferred precursor of phenylacetylglutamine and phenylacetylisoglutamine is 3-phenylacetylamino-2,6-piperidinedione. A preferred precursor of phenylacetic acid for use in the present invention is phenylbutyrate, the structure of which is as follows:

Phenylbutyrate

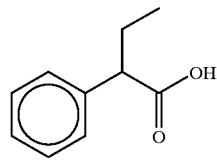

For compounds of Formulas I, III, and IV, purification after synthesis may be required. Any known techniques can be used to purify the desired compound from other compounds and impurities, e.g. HPLC and crystallization from water, among others. The compounds can be quantitated by any known method.

To prepare a pharmaceutical composition of antineoplaston A10, an aqueous solution of sodium phenylacetylglutamine and sodium phenylacetylisoglutamine in a 4:1 ratio is prepared such that the concentration of phenylacetylglutamine in solution is between 160 mg/mL and 280 mg/mL, and preferably between 230 mg/mL and 250 mg/mL; and the concentration of phenylacetylisoglutamine in solution is between 40 mg/mL and 70 mg/mL, and preferably between 55 mg/mL and 65 mg/mL. Preparation of the solution can be performed using any technique known to those skilled in the art. It is to be noted that the solution is to be made sterile, and the pH is to be adjusted to a value at or near the plasma pH of 7.4, e.g. pH 7.0. The active ingredients can be prepared as any compounds of Formulas I and III prior to preparation of the solution, if desired.

To prepare a pharmaceutical composition of antineoplaston AS2-1 according to the present invention, an aqueous solution of sodium phenylacetate and sodium phenylacetylglutamine in a 4:1 ratio by mass is prepared such that the concentration of phenylacetate is between 56 mg/mL and 120 mg/mL, and preferably between 62 mg/mL and 66 mg/mL; and the concentration of phenylacetylglutamine is between 14 mg/mL and 30 mg/mL, and preferably between 15 mg/mL and 17 mg/mL. Preparation of the solution can be performed using any technique known to those of skill in the art. It is to be noted that the solution is to be made sterile, and the pH is to be adjusted to a value at or near the physiological pH of 7.4, e.g. pH 7.0. The active ingredients can be prepared as any compounds of Formulas IV and I prior to preparation of the solution, if such use is desired.

For both antineoplaston A10 and antineoplaston AS2-1, the concentrations of active ingredients used are far greater than those used by any known previously-reported aqueous solution compositions of anti-cancer agents.

Optionally, all compositions according to the present invention can include other agents, such as buffering compounds, glucose, other sugars, preservatives, etc., suitable for use in pharmaceutical compositions prepared for intravenous administration, as are known in the art.

B. Administration of Pharmaceutical Compositions

The pharmaceutical compositions of the present invention are administered intravenously. Methods of intravenous administration are widely known in the art.

In the present invention, the intravenous infusion flow rate of antineoplaston A10 can be between 2.5 mL/h and 400 mL/h for administration to adults and minors. Preferably, the intravenous flow rate is from 100 mL/h to 400 mL/h. Typical flow rates are 250 mL/h for adults and 100–250 mL/h for minors, with flow rates generally greater for older children.

These flow rates are far higher than any known to be previously reported for anti-cancer agents. High flow rates are beneficial in treating cancer because they allow the reaching of blood concentrations of the active agents of antineoplaston A10 roughly twice as high as with conventional lower infusion rates. High flow rates allow reaching of concentrations in the blood which are comparable to those shown to have anti-cancer activity in tissue culture, and also allow superior penetration of tumor tissue. High flow rates are therefore more efficacious than lower infusion rates in the treatment of cancer.

The high flow rate of antineoplaston A10 infusion and the high concentration of antineoplaston A10 produce a diuretic effect. The diuretic effect is beneficial to the patient in preventing fluid overload from large infusion volumes. The diuretic effect is also beneficial to the patient in providing a mechanism for elimination of waste products which can otherwise accumulate in the body.

The antineoplaston A10 composition of the present invention can be administered at the high flow rate of the present invention once or more than once per day, for example, from 4 to 12 times per day, for a period of between 15 min and 24 h. A typical administration regimen is 6 to 8 infusions/day, each infusion of approximately 90 min to 120 min duration.

In the event of a hypersensitivity reaction (usually manifest as a skin rash) by patients to antineoplaston A10, a desensitization protocol may be followed. The total daily dosage is administered in 96 injections (i.e. every 15 min) at a flow rate of 1 mL/min to 4 mL/min (240 mL/h).

The daily dosage level of antineoplaston A10 can be between 0.6 g/kg/day and 25 g/kg/day. Preferably, the daily dosage level of antineoplaston A10 is between 5.0 g/kg/day and 12.0 g/kg/day. Typically, the daily dosage level of antineoplaston A10 is about 8.0 g/kg/day.

The present invention is also directed to intravenous infusion of antineoplaston AS2-1. The intravenous infusion flow rate of antineoplaston AS2-1 can be between 2.5 mL/h and 400 mL/h for administration to adults and can be between 25 mL/h and 400 mL/h for administration to minors. Preferably, the intravenous flow rate is from 100 mL/h to 400 mL/h for adults and minors. Typical flow rates are 250 mL/h for adults and 100–250 mL/h for minors, with flow rates generally greater for older children.

These flow rates are far higher than any known to be previously reported for anti-cancer agents. High flow rates are beneficial in treating cancer because they allow the reaching of blood concentrations of the active agents of antineoplaston AS2-1 roughly twice as high as with conventional lower infusion rates. As described above, high flow rates allow reaching of concentrations in the blood which are comparable to those shown to have anti-cancer activity in tissue culture, and also allow superior penetration of tumor tissue.

The high flow rate of antineoplaston AS2-1 infusion and the high concentration of antineoplaston AS2-1 produce a diuretic effect. The diuretic effect is beneficial to the patient in preventing fluid overload from large infusion volumes and in providing a mechanism for elimination of waste products which can otherwise accumulate in the body, as described above.

The antineoplaston AS2-1 composition of the present invention can be administered at the high flow rate of the present invention once or more than once per day, for example, from 4 to 12 times per day, for a period of between 5 min and 24 h. A typical administration regimen is 6 to 8 infusions/day, each infusion of approximately 10 min to 120 min duration.

In the event of a hypersensitivity reaction (usually manifest as a skin rash) by patients to AS2-1, a desensitization protocol may be followed. The total daily dosage is administered in 96 injections (i.e. every 15 min) at a flow rate of 1 mL/min to 4 mL/min (240 mL/h).

The daily dosage level of antineoplaston AS2-1 can be between 0.1 g/kg/day and 2.6 g/kg/day. Preferably, the daily dosage level of antineoplaston AS2-1 is between 0.2 g/kg/day and 0.9 g/kg/day. Typically, the daily dosage level of antineoplaston A10 is about 0.4 g/kg/day.

The treatment regimen described above is useful in the treatment of patients suffering from all sorts of neoplastic disease, including cancers, both of the hard tissue and soft tissue types, and malignant and benign tumors. In particular, neoplastic diseases that are advantageously susceptible to treatment using the disclosed treatment regimen of this invention include carcinoma of the adrenal gland, carcinoma of the bladder, carcinoma of the breast, high grade glioma, glioblastoma multiforme, astrocytoma including anaplastic and low grade astrocytoma, brain stem glioma, primitive neuroectodermal tumors including medulloblastoma and pinealoblastoma, rhabdoid tumor of the central nervous system, oligodendroglioma, mixed glioma, neurofibroma, schwannoma, visual pathway glioma, ependymoma, germ cell tumors, meningioma, carcinoma of the colon and rectum, carcinoma of the esophagus, primary and metastatic liver cancer, carcinoma of the head and neck, adenocarcinoma of the lung, large cell undifferentiated carcinoma of the lung, bronchio-alveolar carcinoma of the lung, squamous cell carcinoma of the lung, nonsmall cell carcinoma of the lung, non-Hodgkin's lymphomas, chronic leukemias, mesothelioma, malignant melanoma, malignant fibrous histiocytoma, multiple myeloma, neuroblastoma, neuroendocrine tumors, carcinoma of the ovary, carcinoma of the pancreas, primitive neuroectodermal tumors outside the central nervous system, adenocarcinoma of the prostate, carcinoma of the kidney, sarcomas, carcinoma of the small intestine, carcinoma of the stomach, carcinoma of the uterus, carcinoma of the vulva, and carcinoma of an unknown primary.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Forty-three patients diagnosed with primary malignant brain tumors were treated with daily intravenous administration of antineoplaston A10 at an average dosage of 7.9 g/kg/day and antineoplaston AS2-1 at an average dosage of 0.39 g/kg/day. Of the 43 patients, 36 were evaluable, and 16 achieved complete or partial responses by the completion of therapy without serious side effects.

Of the forty-three patients, all but one were diagnosed with histologically confirmed primary brain tumors. The remaining patient suffered from a primary brain tumor in the brain stem where biopsy could not be performed with adequate safety. Fourteen patients were diagnosed with glioblastoma multiforme and six patients were diagnosed with anaplastic astrocytoma.

Patients ranged in age from 2 to 71. Patients were selected for Karnofsky Performance Status of 40 to 100, life expectancy over two months, and age over 1 year. Patients with liver failure, hypertension not adequately controlled, or who were pregnant or breastfeeding were excluded. All patients had previously undergone surgery or chemotherapy and/or radiation therapy with negative result.

The formulation of antineoplaston A10 was made as described above, with between 230 mg/mL and 250 mg/mL of phenylacetylglutamine and between 55 mg/mL and 65 mg/mL of phenylacetylisoglutamine and adjusted to pH 7.0. The formulation of antineoplaston AS2-1 was made as described above, with between 62 mg/mL and 66 mg/mL of sodium phenylacetate and between 15 mg/mL and 17 mg/mL of phenylacetylglutamine, and adjusted to pH 7.0.

Patients received intravenous injections of the antineoplastons through a single-lumen subclavian catheter (Broviac, Groshong, or equivalent). Patients received gradually escalating doses by multiple intermittent injections using a portable Abbott Provider 6000 dual-channel programmable pump six times per day. Infusion rates for adults were 250 mL/h and for persons under 18 the infusion rates were 50–100 mL/h, depending on tolerance. Infusions were administered for periods ranging from 91 days to 3509 days, with a median duration of treatment of 661 days. The average dosage of antineoplaston A10 was 7.91 g/kg/day and the average dosage of AS2-1 was 0.39 g/kg/day. The maximum total dose of antineoplaston A10 was 551.865 kg and the maximum total dose of AS2-1 was 59.348 kg.

Before beginning treatment, evaluable patients had recovered completely from surgery, if performed, or had discontinued chemotherapy for at least 4 weeks (6 weeks if chemotherapy consisted of nitrosoureas) and/or had discontinued radiation therapy for at least 6 weeks.

A complete response was judged as a complete disappearance of all contrast-enhancing tumors on imaging studies (MRI, etc.) for four weeks or longer. A partial response was judged as a more than 50% reduction in the sum of the products of the greatest perpendicular diameters of contrast-enhancing tumors for at least 4 weeks without the appearance of new lesions.

A state of stable disease was judged as a less than a 50% change (either increase or decrease) in the sum of the products of the greatest perpendicular diameters of contrast-enhancing tumors for a minimum of 12 weeks. A state of progressive disease was judged as a greater than 50% increase in the sum of the products of the greatest perpendicular diameters of contrast-enhancing tumors, or the appearance of new lesions.

Of the 36 evaluable patients, 7 (19.5%) obtained complete responses. Nine patients (25%) obtained partial response. Stable disease was observed for 12 patients (33.3%). Progressive disease developed for 8 patients (22.2%).

A number of adverse drug experiences were noted during the trial, including hypernatremia, hypochloremia, hyperchloremia, hypokalemia, skin rash, somnolence, weakness, nausea and vomiting, headaches, slurred speech, confusion, hallucination, fever, and fluid retention. The majority of adverse drug experiences were mild and did not significantly interrupt the treatment program. For example, there were 23 cases of hypematremia not higher than 150 mEq/L, twelve cases not higher than 160 mEq/L, and two cases not higher than 170 mEq/L. Hypochloremia was identified in six cases and hyperchloremia in two cases. There were seven cases of hypokalemia not lower than 2.8 mEq/L. The dose-limiting factor for antineoplaston A10 appeared to be the volume of intravenous fluid, and for AS2-1 the dose-limiting factor is increased sleepiness and weakness.

Of the 16 patients classified as experiencing complete or partial responses, 13 remain alive, as are eight patients classified as stable disease, progressive disease, and non-evaluable. The majority of surviving patients are now alive for over four years since pathology diagnosis, and two patients, one suffering from oligodendroglioma and one from low-grade astrocytoma, have survived approximately 12 years since pathology diagnosis.

Therefore, treatment of cancer by intravenous administration of highly concentrated aqueous solutions of antineoplaston A10 and antineoplaston AS2-1 at high flow rates and high daily dosages according to the present invention resulted in partial or complete response in almost 50% of evaluable patients with minimal adverse drug experiences.

EXAMPLE 2

A Phase II clinical study of antineoplaston A10 and AS2-1 was conducted in twelve patients with high grade glioma. Seven patients were diagnosed with glioblastoma multiforme, four patients were diagnosed with anaplastic astrocytoma, and one patient was diagnosed with brain stem glioma with multiple metastases.

Patients received continuous infusions of antineoplaston A10 and AS2-1 for from 41 days to 713 days. Dosage levels of antineoplaston A10 were from 0.9 g/kg/day to 1.7 g/kg/day, and dosage levels of AS2-1 were from 0.2 g/kg/day to 0.8 g/kg/day.

Adverse drug experiences of mild nature and sporadic occurrence were noted in five patients in the trial. Two patients exhibited a mild, temporary decrease in white blood cell count and one patient exhibited a temporary decrease in red blood cell count and hemoglobin. Two patients had hypokalemia and hypoglycemia, one patient had increased fluid retention, and one patient had stomach cramps and nausea once during treatment.

Complete response was observed in two patients, and partial response was noted in two patients. Four patients experienced stabilization, and four patients experienced progressive disease.

EXAMPLE 3

A Phase II study of antineoplaston A10 and AS2-1 was conducted on 11 patients with brain tumors. Dosage levels of antineoplaston A10 were from 3.9 g/kg/day to 12.9 g/kg/day, and dosage levels of AS2-1 were from 0.20 g/kg/day to 0.40 g/kg/day. Eight patients were evaluable. Partial response was observed for five patients by the completion of treatment.

Patients suffered from brain tumors. Injections of antineoplaston A10 and AS2-1 were administered 6×daily at 250 mL/h using a subclavian catheter and double channel infusion pump as described in Example 1. The duration of treatment ranged from 44 days to 480 days, with a median duration of treatment of 195 days. Dosage levels of antineoplaston A10 were from 3.9 g/kg/day to 12.9 g/kg/day with an average dosage of 7.2 g/kg/day. Dosage levels of AS2-1 were from 0.20 g/kg/day to 0.40 g/kg/day, with an average dosage of 0.29 g/kg/day. The maximum total dose of antineoplaston A10 was 381.738 kg and the maximum total dose of AS2-1 was 9.702 kg.

Of the eight evaluable patients in the study, partial response was observed for five patients, stable disease was observed in two patients, and one patient developed progressive disease.

Several possible adverse drug experiences were identified, consisting of hypernatremia, hypochloremia, elevated creatinine, allergy, somnolence, weakness, fever, and arthralgia. The adverse drug experiences were mild and did not have significant impact on continuation of treatment; specifically, there were two cases of hypernatremia not higher than 150 mEq/L and four cases not higher than 160 mEq/L. One case of hypochloremia was identified at 82 mEq/L, as were three cases of hypokalemia not lower than 2.5 mEq/L.

Therefore, treatment of cancer by intravenous administration of highly concentrated aqueous solutions of antineoplaston A10 and antineoplaston AS2-1 at high flow rates and high daily dosages according to the present invention resulted in partial or complete response in 62.5% of evaluable patients with minimal adverse drug experiences.

EXAMPLE 4

A Phase II study of antineoplaston A10 and AS2-1 was conducted on 15 patients with brain stem glioma. Dosage levels of antineoplaston A10 ranged from 5.27 g/kg/day to 16.06 g/kg/day, and dosage levels of AS2-1 ranged from 0.20 g/kg/day to 0.57 g/kg/day. Complete response was observed in two patients and two patients obtained partial response.

Fifteen patients suffering from brain stem gliomas accrued to the study, of whom 14 were evaluable. Patients received injections of antineoplaston A10 and AS2-1 6×daily as described in Examples 1. Dosage levels of antineoplaston A10 ranged from 5.27 g/kg/day to 16.06 g/kg/day, with an average dosage of 9.47 g/kg/day. Dosage levels of AS2-1 ranged from 0.20 g/kg/day to 0.57 g/kg/day, with an average dosage of 0.37 g/kg/day. The maximum total dose of antineoplaston A10 was 311.985 kg and of AS2-1, 9.912 kg.

Of the 14 evaluable patients, complete response was observed in two patients and two patients obtained partial response, according to the definitions given in Example 1. Stable disease was observed in five patients, and five patients developed progressive disease.

Several adverse drug experiences possibly related to the treatment with antineoplaston A10 and AS2-1 were identified. These consisted of hypernatremia, hypokalemia, allergic skin rash, elevated transaminases, somnolence, weakness, dyspnea, nausea and vomiting, diarrhea, fever, and arthralgia. There were eight cases of hypernatremia not higher than 150 mEq/L, three cases not higher than 165 mEq/L, and one case of 189 mEq/L. Hypokalemia not lower than 2.5 mEq/L was identified in two cases. Adverse drug experiences were mild and did not have significant impact on continuation of treatment.

Therefore, treatment of cancer by intravenous administration of highly concentrated aqueous solutions of antineoplaston A10 and antineoplaston AS2-1 at high flow rates and high daily dosages according to the present invention resulted in partial or complete response in almost 30% of evaluable patients with minimal adverse drug experiences.

EXAMPLE 5

A Phase II study of antineoplaston A10 and AS2-1 was conducted on 12 adult patients with mixed glioma. Nine patients were evaluable. Dosage levels of antineoplaston A10 were from 3.5 g/kg/day to 12.1 g/kg/day, and dosage levels of AS2-1 ranged from 0.24 g/kg/day to 0.40 g/kg/day. Of nine evaluable patients, complete responses were determined in three patients and one patient obtained a partial response.

Patients received injections of antineoplaston A10 and AS2-1 as described in Example 1. The duration of treatment ranged from 32 days to 615 days, with a median duration of treatment of 191 days. Dosage levels of antineoplaston A10 were from 3.5 g/kg/day to 12.1 g/kg/day, with an average dosage level of 7.6 g/kg/day. Dosage levels of AS2-1 were from 0.24 g/kg/day to 0.40 g/kg/day, with an average dosage level of 0.33 g/kg/day. The maximum total dose of antineoplaston A10 was 192.907 kg, and for AS2-1 was 11.189 kg.

Of the 12 patients, nine were evaluable. Of these nine, complete responses were determined in three patients and one patient obtained a partial response, according to the definitions given in Example 1. Stable disease was observed for two patients, and three patients developed progressive disease.

Several adverse drug experiences were encountered that were possibly related to treatment with antineoplaston A10 and AS2-1. These consisted of hypernatremia, hyperchloremia, hypokalemia, diarrhea, and nausea. There were eight cases of hypernatremia not higher than 150 mEq/L and two cases not higher than 160 mEq/L. Hyperchloremia of 111 mEq/L and hypokalemia of 3.1 mEq/L were observed in one case each. Adverse drug experiences were mild and did not have a significant impact on continuation of administration of antineoplastons.

Summary of Toxicity Observations in Clinical Trials

The incidence of adverse drug experiences was analyzed from data collected from 1,003 patients with various types of malignancies enrolled in 67 Phase II study protocols approved by the FDA. Some, but not all, of the Phase II protocols are described in detail in the Examples above. Because in many cases the patients who participated in the clinical studies suffered from advanced cancers with short life expectancies, it was often difficult to identify if the side effects were due to the advanced stage of the diseases or to the antineoplaston treatment regimen. In any event, only 1.7% of patients experienced serious (Grade 3 or 4) toxicity.

In Phase II clinical trials of antineoplaston A10 and AS2-1, and also special exceptions, 0.3% of patients experienced Grade 4 toxicity, specifically single cases of hypernatremia, thrombocytopenia and hyperbilirubinemia. 1.4% of patients experienced Grade 3 toxicity, specifically hypernatremia, hypocalcemia, hypokalemia, hypomagnesemia, elevation of SGOT, or elevation of SGPT.

Grade 2 toxicity was observed in 18.6% of patients, and included fever in the absence of infection (3.3%), hypokalemia (3.0%), hypernatremia (2.0%), hypochloremia (1.9%), and neurocortical symptoms such as confusion and sleepiness (1.5%). Between 0.5% and 0.9% of patients experienced allergy, hypomagnesemia, neurohearing symptoms, vomiting, neurocerebellar symptoms such as dizziness and slurred speech, nausea, or hyperchloremia. Less than 0.5% of patients experienced decreased hemoglobin, hypocalcemia, increase of SGPT, fluid retention, neuromotor weakness, or neurovision symptoms; single cases of chills, diarrhea, granulocytopenia, leucopenia, lymphocytopenia, headache, polyneuropathy, and elevation of SGOT were also observed.

Grade 1 toxicity in the form of laboratory abnormalities and minor symptoms was experienced by the majority of patients, including hypematremia (54.3%), hypokalemia (18.0%), allergy (14.2%), neurocortical symptoms (9.1%), neuromotor weakness (7.8%), vomiting (7.6%), hypochloremia (7.1%), nausea without vomiting (6.8%), and fever in the absence of infection (6.0%). Local toxicity was observed in 7.5% of patients, most commonly as arthralgia, with myalgia, arthritis, and erythema nodosum also observed.

Additional Grade 1 toxicity was observed for between 1.0% and 5.0% of patients with hyperchloremia, headache, neurocerebellar symptoms, diarrhea, fluid retention, hypomagnesemia, neurohearing symptoms, hyponatremia, and pulmonary dyspnea. Rare (less than 1.0%) adverse drug experiences included hypocalcemia, chills, constipation, neurovision symptoms, SGOT and SGPT elevation, hypertension, increased epidermization, thrombocytopenia, and single cases of elevated alkaline phosphatase, bilirubin, creatinine, or granulocytopenia, decreased hemoglobin, and hypercalcemia.

Almost all patients experienced increased diuresis (98.3%) and slight thirst, most likely explained by administration of large volumes of intravenous fluids. The high incidence of hypernatremia is most likely explained by intake of the antineoplastic compounds as sodium salts, dehydration, and malignant tumors, especially brain and liver tumors.

The maximum dosages administered were 25 g/kg/day of antineoplaston A10, and 2.59 g/kg/day of AS2-1.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Burzynski, U.S. Pat. No. 4,470,970
Burzynski et al. *Drugs Exptl. Clin. Res.* 12 Suppl. 1, 25–35 (1986)
Burzynski et al. (*Drugs Exptl. Clin. Res.* 12 Suppl. 1, 11–16 (1986))
Samid, U.S. Pat. No. 5,605,930

What is claimed is:

1. A method of treating a neoplastic disease in a patient in need thereof, wherein the neoplastic disease is selected from the group consisting of: carcinoma of the adrenal gland, carcinoma of the bladder, carcinoma of the breast, high grade glioma, glioblastoma multiforme, anaplastic astrocytoma, low grade astrocytoma, brain stem glioma, primitive neuroectodermal tumors, medulloblastoma, pinealoblastoma, rhabdoid tumor of the central nervous stystem, oligodendroglioma, mixed glioma, neurofibroma, schwannoma, visual pathway glioma, ependymoma, germ cell tumors, meningioma, carcinoma of the colon, carcinoma of the rectum, carcinoma of the esophagus, primary liver cancer, metastatic liver cancer, carcinoma of the head, carcinoma of the neck, adenocarcinoma of the lung, large cell undifferentiated carcinoma of the lung, bronchioalveolar carcinoma of the lung, squamous cell carcinoma of the lung, nonsmall cell carcinoma of the lung, non-Hodgkin's lymphoma, chronic leukemia, mesothelioma, malignant melanoma, malignant fibrous histiocytoma, multiple myeloma, neuroblastoma, a neuroendocrine tumor, carcinoma of the ovary, carcinoma of the pancreas, a primitive neuroectodermal tumor outside the central nervous system, adenocarcinoma of the prostate, carcinoma of the kidney, sarcoma, carcinoma of the small intestine, carcinoma of the stomach, carcinoma of the uterus, carcinoma of the vulva, and carcinoma of an unknown primary source; the method comprising:

administering to the patient first and second pharmaceutical compositions, each at an infusion rate of from about 100 mL/hr to about 400 mL/hr, the first pharmaceutical composition comprising an aqueous solution of a compound of Formula IV:

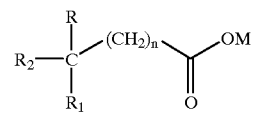

wherein R and $R_1$ are independently selected from the group consisting of H, lower alkoxy ($C_{1-6}$), and lower alkyl ($C_{1-6}$); $R_2$ is selected from Formula II:

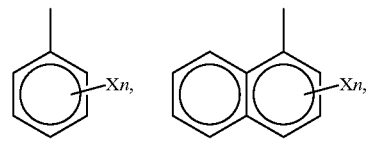

wherein X is a halogen, lower alkyl ($C_{1-6}$), lower alkoxy ($C_{1-6}$) cycloalkyl, cycloalkoxy, aryl, substituted aryl ($C_{6-12}$) or hydroxy and n is 0, 1, 2, 3, or 4; M is hydrogen, a salt forming cation, alkyl ($C_{1-6}$), cycloalkyl, or aryl ($C_{6-12}$); and n is 0–5; and, a compound of Formula I:

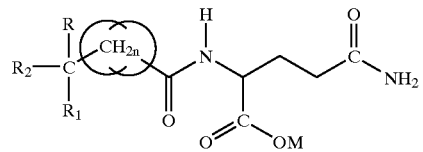

wherein n is 0, 1, 2, 3, 4, or 5; M is hydrogen, a salt forming cation, an alkyl ($C_{1-6}$), a cycloalkyl, or an aryl ($C_{6-12}$); R and $R_1$ are independently selected from the group consisting of H, lower alkoxy ($C_{1-6}$), and lower alkyl ($C_{1-6}$); $R_2$ is selected from Formula II, as defined above;

and a second pharmaceutical composition, comprising a compound of Formula I wherein n is 0, 1, 2, 3, 4, or 5; M is hydrogen, a salt forming cation, an alkyl ($C_{1-6}$), a cycloalkyl, or an aryl ($C_{6-12}$); R and $R_1$ are independently selected from the group consisting of H, lower alkoxy ($C_{1-6}$) and lower alkyl ($C_{1-6}$); $R_2$ is selected from Formula II, as defined above; and a compound of Formula III

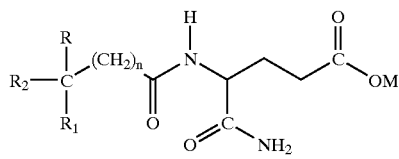

wherein n is 0, 1, 2, 3, 4, or 5; M is hydrogen, a salt forming cation, an alkyl ($C_{1-6}$), a cycloalkyl, or an aryl ($C_{6-12}$); R and $R_1$ are independently selected from the group consisting of H, lower alkoxy ($C_{1-6}$), and lower alkyl ($C_{1-6}$); $R_2$ is selected from Formula II as defined above;

wherein in the first pharmaceutical composition the compound of Formula IV and the compound of Formula I are present in a 4:1 ratio by weight, and the combined concentration of the compound of Formula IV and the compound of Formula I is from about 70 mg/mL to about 150 mg/mL; and wherein, in the second pharmaceutical composition, the compound of formula I and the compound of formula III are present in a 4:1 ratio and the combined concentration of the compounds of formula I and formula III is from about 200 mg/mL to about 350 mg/mL.

2. The method of claim 1, wherein the infusion rate is about 250 mL/hr to about 300 mL/hr, and further comprising performing the administering step sufficiently often to reach a dosage level of from about 0.1 g/kg/day to about 2.6 g/kg/day for the first pharmaceutical composition and from about 0.6 g/kg/day to about 25 g/kg/day for the second pharmaceutical composition.

3. The method of claim 2, wherein the dosage level is from about 0.2 g/kg/day to about 0.9 g/kg/day for the first pharmaceutical composition and from about 5.0 g/kg/day to about 12.0 g/kg/day for the second pharmaceutical composition.

4. The method of claim 1, wherein in the compound of Formula IV, M is hydrogen or sodium; n is 0; R is H or $C_3H_7$; $R_1$ is selected from the group consisting of H, $CH_3$, $CH_3$—O—, $C_2H_5$, and $C_3H_7$; $R_2$ is selected from Formula II, wherein X is Cl, F, or OH; and wherein in the compounds of Formula I and III, M is hydrogen or sodium; n is 0; R is H or $C_3H_7$; $R_1$ is selected from the group consisting of H, $CH_3$, $CH_3$—O—, $C_2H_5$, and $C_3H_7$; $R_2$ is selected from Formula II, wherein X is Cl, F, or OH.

5. The method of claim 1, wherein the compound of Formula IV is phenylacetic acid or a pharmaceutically acceptable salt thereof, the compound of Formula I is phenylacetylglutamine or a pharmaceutically acceptable salt thereof, and the compound of Formula III is phenylacetylisoglutamine or a pharmaceutically acceptable salt thereof.

6. The method of claim 5, wherein the combined concentration of the compounds of formula IV and formula I in the first pharmaceutical composition is about 80 mg/mL.

7. The method of claim 1 wherein the pharmaceutical composition comprises a compound of formula I selected from phenylacetylglutamine or a pharmaceutically acceptable salt thereof.

8. The method of claim 1 wherein the pharmaceutical comprises a compound of formula III selected from phenylacetylisoglutamine or a pharmaceutically acceptable salt thereof.

9. A method of treating a neoplastic disease in a patient in need thereof, wherein the neoplastic disease is selected from the group consisting of: carcinoma of the adrenal gland, carcinoma of the bladder, carcinoma of the breast, high grade glioma, glioblastoma multiforme, anaplastic astrocytoma, low grade astrocytoma, brain stem glioma, primitive neuroectodermal tumors, medulloblastoma, pinealoblastoma, rhabdoid tumor of the central nervous stystem, oligodendroglioma, mixed glioma, neurofibroma, schwannoma, visual pathway glioma, ependymoma, germ cell tumors, meningioma, carcinoma of the colon, carcinoma of the rectum, carcinoma of the esophagus, primary liver cancer, metastatic liver cancer, carcinoma of the head, carcinoma of the neck, adenocarcinoma of the lung, large cell undifferentiated carcinoma of the lung, bronchioalveolar carcinoma of the lung, squamous cell carcinoma of the lung, nonsmall cell carcinoma of the lung, non-Hodgkin's lymphoma, chronic leukemia, mesothelioma, malignant melanoma, malignant fibrous histiocytoma, multiple myeloma, neuroblastoma, a neuroendocrine tumor, carcinoma of the ovary, carcinoma of the pancreas, a primitive neuroectodermal tumor outside the central nervous system, adenocarcinoma of the prostate, carcinoma of the kidney, sarcoma, carcinoma of the small intestine, carcinoma of the stomach, carcinoma of the uterus, carcinoma of the vulva, and carcinoma of an unknown primary source; the method comprising:

administering to the patient first and a second pharmaceutical compositions, each composition administered at an infusion rate of from about 100 mL/hr to about 400 mL/hr, the first pharmaceutical composition comprising an aqueous solution of a compound of Formula IV:

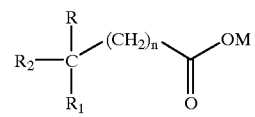

wherein R and $R_1$ are independently selected from the group consisting of H, lower alkoxy ($C_{1-6}$), and lower alkyl ($C_{1-6}$); $R_2$ is selected from Formula II:

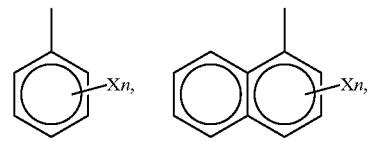

wherein X is a halogen, lower alkyl ($C_{1-6}$) lower alkoxy ($C_{1-6}$), cycloalkyl, cycloalkoxy, aryl, substituted aryl ($C_{6-12}$) or hydroxy and n is 0, 1, 2, 3, or 4; M is hydrogen, a salt forming cation, alkyl ($C_{1-6}$), cycloalkyl, or aryl ($C_{6-12}$); and n is 0–5; and, Formula III

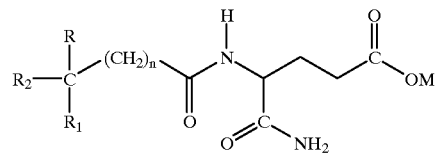

wherein n is 0, 1, 2, 3, 4, or 5; M is hydrogen, a salt forming cation, an alkyl ($C_{1-6}$), a cycloalkyl, or an aryl ($C_{6-12}$); R and $R_1$ are independently selected from the group consisting of H, lower alkoxy ($C_{1-6}$), and lower alkyl ($C_{1-6}$); $R_2$ is selected from Formula II, as defined above;

and a second pharmaceutical composition, comprising:
a compound of Formula I:

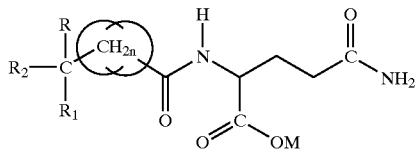

wherein n is 0, 1, 2, 3, 4, or 5; M is hydrogen, a salt forming cation, an alkyl ($C_{1-6}$), a cycloalkyl, or an aryl ($C_{6-12}$); R and $R_1$ are independently selected from the group consisting of H, lower alkoxy ($C_{1-6}$), and lower alkyl ($C_{1-6}$); $R_2$ is selected from Formula II, as defined above; and a compound of Formula III

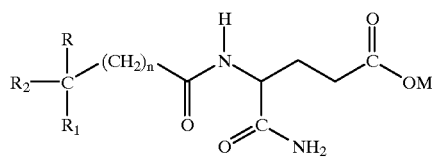

wherein n is 0, 1, 2, 3, 4, or 5; M is hydrogen, a salt forming cation, an alkyl ($C_{1-6}$), a cycloalkyl, or an aryl ($C_{6-12}$); R and $R_1$ are independently selected from the group consisting of H, lower alkoxy ($C_{1-6}$), and lower alkyl ($C_{1-6}$) $R_2$ is selected from Formula II, as defined above;

wherein in the first pharmaceutical composition the compound of Formula IV and the compound of Formula III are present in a 4:1 ratio by weight, and the combined concentration of the compound of Formula IV and the compound of Formula I or III is from about 70 mg/mL to about 150 mg/mL; and wherein in the second pharmaceutical composition the compound of formula I and the compound of formula III are present in a 4:1 ratio and the combined concentration of the compounds of formula I and formula III is from about 200 mg/mL to about 350 mg/mL.

10. The method of claim 9, wherein the infusion rate is about 250 mL/hr to about 300 mL/hr, and further comprising performing the administering step sufficiently often to reach a dosage level of from about 0.1 g/kg/day to about 2.6 g/kg/day for the first pharmaceutical composition and from about 0.6 g/kg/day to about 25 g/kg/day for the second pharmaceutical composition.

11. The method of claim 10, wherein the dosage level is from about 0.2 g/kg/day to about 0.9 g/kg/day for the first pharmaceutical composition and from about 5.0 g/kg/day to about 12.0 g/kg/day for the second pharmaceutical composition.

12. The method of claim 9, wherein in the compound of Formula IV, M is hydrogen or sodium; n is 0; R is H or $C_3H_7$; $R_1$ is selected from the group consisting of H, $CH_3$, $CH_3$—O—, $C_2H_5$, and $C_3H_7$; $R_2$ is selected from Formula II, wherein X is Cl, F, or OH; and wherein in the compounds of Formula I and III, M is hydrogen or sodium; n is 0; R is H or $C_3H_7$; $R_1$ is selected from the group consisting of H, $CH_3$, $CH_3$—O—, $C_2H_5$, and $C_3H_7$; $R_2$ is selected from Formula II, wherein X is Cl, F, or OH.

13. The method of claim 9, wherein the compound of Formula IV is phenylacetic acid or a pharmaceutically acceptable salt thereof, the compound of Formula I is phenylacetylglutamine or a pharmaceutically acceptable salt thereof, and the compound of Formula III is phenylacetylisoglutamine or a pharmaceutically acceptable salt thereof.

14. The method of claim 13, wherein the combined concentration of the compounds of formula IV and formula III in the first pharmaceutical composition is about 80 mg/mL.

15. The method of claim 9 wherein the compound of formula I selected from phenylacetylglutamine or a pharmaceutically acceptable salt thereof.

16. The method of claim 9 wherein the compound of formula III selected from phenylacetylisoglutamine or a pharmaceutically acceptable salt thereof.

* * * * *

UNITED STATES PATENT AND TRADEMARK OFFICE
CERTIFICATE OF CORRECTION

PATENT NO. : 6,943,192 B2
DATED : September 13, 2005
INVENTOR(S) : Stanislaw R. Burzynski It is certified that error appears in the above-identified patent and that said Letters Patent is hereby corrected as shown below:

Column 18,
Lines 46-53, please replace the formula with the following formula:

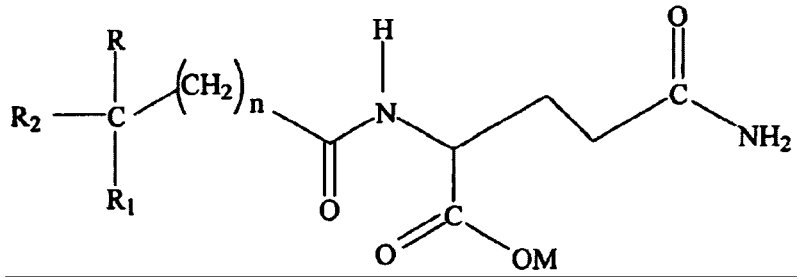

Column 19,
Line 51, "phenylacetylgiutamine" should read -- phenylacetylglutamine --.

Signed and Sealed this

Twentieth Day of December, 2005

JON W. DUDAS
*Director of the United States Patent and Trademark Office*